United States Patent [19]
Masini

[11] Patent Number: 5,976,149
[45] Date of Patent: Nov. 2, 1999

[54] METHOD AND APPARATUS FOR ALIGNING A PROSTHETIC ELEMENT

[75] Inventor: Michael A. Masini, Ann Arbor, Mich.

[73] Assignee: MedIdea, LLC, Ann Arbor, Mich.

[21] Appl. No.: 09/021,218

[22] Filed: Feb. 10, 1998

Related U.S. Application Data

[60] Provisional application No. 60/037,669, Feb. 11, 1997.

[51] Int. Cl.[6] .................................................. A61B 17/88
[52] U.S. Cl. .............................................. 606/91; 623/22
[58] Field of Search ................................ 606/53, 81, 86, 606/91, 92, 99; 623/22, 23; 422/99, 104

[56] References Cited

U.S. PATENT DOCUMENTS

| | | | |
|---|---|---|---|
| 3,067,740 | 12/1962 | Haboush | 623/22 |
| 5,037,424 | 8/1991 | Aboczsky | 606/91 |
| 5,116,339 | 5/1992 | Glock | 606/91 |
| 5,141,512 | 8/1992 | Farmer et al. | 606/87 |
| 5,501,687 | 3/1996 | Willert et al. | 606/94 |
| 5,527,317 | 6/1996 | Ashby et al. | 606/91 |

*Primary Examiner*—Michael Buiz
*Assistant Examiner*—David O. Reip
*Attorney, Agent, or Firm*—Gifford, Krass, Groh, Sprinkle, Anderson & Citkowski, PC

[57] ABSTRACT

Methods and apparatus facilitate the positioning of a prosthetic element relative to a bone so as to achieve a desired orientation. An anchoring unit rigidly attaches to a point of the bone surrounding a region associated with receiving the prosthetic element, and at least one structural member is used to physically couple the prosthetic element to the anchoring unit. The combination of the anchoring unit and structural member includes one or more fasteners which may be loosened to temporarily remove the prosthetic element once a desired orientation is achieved, while facilitating re-installation of the element in accordance with the desired orientation following the temporary removal. In a preferred embodiment, the prosthetic element is an acetabular implant, and the surrounding bone forms part of a human pelvis. Regardless of the application, the element may take the form of a trial or a final implant.

6 Claims, 3 Drawing Sheets

5,976,149

METHOD AND APPARATUS FOR ALIGNING A PROSTHETIC ELEMENT

REFERENCE TO RELATED APPLICATION

This application claims priority of U.S. provisional application Ser. No. 60/037,669, filed Feb. 11, 1997, the entire contents of which are incorporated herein by reference.

FIELD OF THE INVENTION

This invention relates generally to the field of prosthetics and, in particular, to methods and apparatus for positioning an implant relative to a bone so as to achieve a desired orientation. More specifically, the invention is directed toward instrumentation and surgical techniques which ensure an accurately aligned acetabular prosthetic element.

BACKGROUND OF THE INVENTION

Improved orthopedic procedures have made joint replacement and augmentation techniques commonplace. In total hip arthroplasty, both the femoral or ball aspect of the joint as well as the acetabular or socket portion are replaced with prosthetic implants. A wealth of references exist in this field, and many patents have been issued with respect to the implants themselves, as well as the tools used in such procedures and various methods associated with such procedures.

Although different techniques have been proposed to ensure correct placement of the femoral portion of a hip replacement, techniques associated with the implantation of acetabular prostheses are far less developed. There are several reasons for the lack of progress in this area. First, perhaps, exposure and resection of the femoral shaft is surgically more straightforward, facilitating a wider variety of alignment procedures. Access to the acetabulum is more challenging since the pelvic region, unlike the femoral counterpart, is relatively stationary during surgery, and the bones comprising the socket region to accept the implant are geometrically more complex, particularly if considerable deterioration or deformity are present.

This situation has led to the use of imperfect techniques associated with prosthetic acetabula implantation, often involving the use of manually operated instrumentation which relies only on the surgeon's hand and eye coordination to install the implant, occasionally relying upon visual markers. Existing tools in this area are described in U.S. Pat. Nos. 5,037,424, 5,116,339, 5,141,512, and 5,527,317.

With the increasing awareness that alignment accuracy fosters implant longevity, the need remains for instrumentation and/or techniques associated with the positioning an implant relative to a bone so as to achieve a desired orientation. Such advances could assist in the alignment of the acetabular component during hip arthroplasty, for example, to ensure a co-acting joint which more faithfully reproduces natural movements and reduces complications such as dislocation and wear.

SUMMARY OF THE INVENTION

The present invention resides in apparatus and associated methods for positioning a prosthetic element relative to a bone so as to achieve a desired orientation. Broadly, an anchoring unit rigidly attaches to a point of the bone surrounding a region associated with receiving the prosthetic element, and at least one structural member is used to rigidly couple the prosthetic element to the anchoring unit. The combination of the anchoring unit and structural element preferably includes one or more fasteners which may be loosened to temporarily remove the prosthetic element once a desired orientation is achieved, while facilitating re-installation of the element in accordance with the desired orientation following the temporary removal. In a preferred embodiment, the prosthetic element is an acetabular implant, and the surrounding bone forms part of a human pelvis.

Regardless of the application, the element may take the form of a trial or a final implant. More particularly, the prosthetic element may be a non-final implant of the type provided and used for trialing or "fitting" purposes, which would require replacement with a final implant prior to fixation. In the alternative, the final implant itself may provide means facilitating a temporary connection thereto, or the invention may grasp the final implant in some manner, enabling the final itself to be used for trialing purposes prior to its own fixation. Given this versatility of the invention, use of the term "implant" should be taken to mean the final implant adapted for fixation or any other device shaped at least partially like the final for test purposes. In addition, although reference is made herein to cementation, it will be noted and understood by those of skill given applicant's specification that non-cemented implants may be utilized as well, including those having surfaces adapted for bone ingrowth.

In certain configurations the apparatus includes one or more adjustment devices enabling the anchoring unit to be moveably positioned prior to its rigid attachment to the surrounding bone while the prosthetic element remains in position at the desired orientation. In this case, the apparatus preferably features a plurality of such adjustment devices, facilitating a multidimensional desired orientation of the prosthetic element. The anchoring unit may conveniently include a sleeve through which a threaded rod may be removably inserted into the surrounding bone, thus providing an exposed post over which the sleeve of the anchoring unit may be removably installed.

If cementation of the final implant is used, apparatus according to the invention may further include devices to facilitate the formation of a uniform-thickness cement mantle, which has been shown to promote implant stability. In one embodiment of this aspect of the invention, an implant having an outer lip is provided which covers the surrounding bone immediately adjacent to the region associated with receiving the prosthetic element. One or more cement injection ports, and one or more cement release ports are provided, enabling the cement to be injected with the implant in place. Such release ports may be designed to expel cement upon the occurrence a cement over-pressurization. In an alternative embodiment of this aspect of the invention, a cup-shaped cement injection device is provided, which is temporarily inserted into the socket then removed, leaving a substantially uniform-thickness uncured cement bed into which a final implant is urged until fixation occurs.

A method aspect associated with the positioning of a prosthetic element relative to a bone so as to achieve a desired orientation according to the invention includes the steps of attaching an anchoring unit to surrounding bone, including an adjustable structural assembly having an end adapted for attachment to the prosthetic element; adjusting the orientation of the prosthetic element relative to the bone with the structural assembly attached thereto; and locking the prosthetic element into position once achieving the desired orientation. Importantly, the steps of adjusting the orientation of the prosthetic element and locking the prosthetic element into position may be performed as part of a joint reduction, enabling modification to permit optimal re-positioning, as desired.

DETAILED DESCRIPTION OF THE PREFERRED EMBODIMENTS

Figure 1:
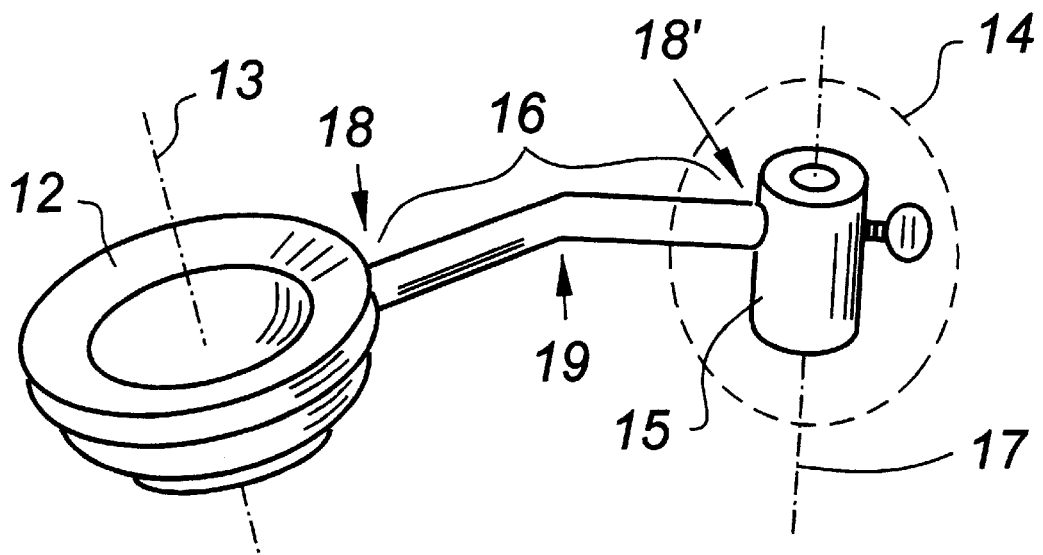
FIG. 1 illustrates, from an oblique perspective, an alignment device according to this invention.

FIG. 1 illustrates a basic embodiment of the invention. Broadly, an acetabular implant 12 is connected to a bone-anchoring unit 14 through a structural member 16 which acts as an outrigger. The implant 12 may either be of the type used in trialing, or may be a final prosthetic device. Accordingly, the item 12 may be fashioned from a number of materials, including metal alloys and/or polymerics, most notably polyethylene. If the item 12 is symmetrical, such symmetry may occur with respect to an axis 13. As will become clear, the invention is not limited to any particular material or material combinations, nor is the invention limited to the hip in general or the acetabulum in particular, as the principles disclosed herein may find widespread use in any orthopedic situation which would benefit from accurate alignment or orientation.

In the preferred embodiment, the anchoring unit 14 takes the form of a sleeve 15 defining an axis 17 which is rigidly connected to the member 16. This particular configuration enables the bore of the sleeve 15 to function as a guide for a drill or a threaded pin (not shown) adapted for fixation into surrounding bone along the axis 17, as better visualized in FIG. 2A. It will be appreciated, however, that various other anchoring units fall within the scope of the invention, with the only requirement being that the implant or trial be rigidly and temporarily secured to an area of the surrounding bone. Note also that whereas the axis 13 of the trial or final implant 12 and axis 17 of the sleeve 15 are shown in FIG. 1 as non-parallel, a parallel arrangement is also possible and may be desirable in some circumstances.

The member 16 has a first end connected to the implant 12 at point 18, and the second end connected to the bone-anchoring unit at 18'. The member is depicted with a bend 19 along its length, to better geometrically configure this particular anchoring arrangement, though it should be kept in mind that different physical realizations of the member may be used including straight or curved variations and segments, depending upon various factors such as the type of anchoring mechanism utilized and the particular orthopaedic situation. Additionally, although the connections at point 18 and 18' are shown as rigid connections, they may be made adjustable, as shown in FIG. 2, for example, to provide for a more flexible arrangement prior to being locked into position.

With respect to the invention being adapted to temporarily connect to a conventionally available final implant, the attachment to the implant may employ jaws or other means to connect to an outer rim of either the existing cementable or non-cemented final implant now being offered or which may be offered in the future. As an alternative, a ball-shaped holding member may be used which fits into the socket of the trial or implant and expands or otherwise grabs the socket until fixation occurs. In the case of a non-cemented implant, temporary clamping may take place with respect to the rigid ring which into which a polymeric insert is snapped into place.

Making particular reference now to FIG. 1A, there is shown an embodiment of the invention which is adjustably lockable along a greater number of degrees of freedom as compared to the embodiment of FIG. 1. In this case, the sleeve 20 has been used as a guide through which a threaded rod 22 has been inserted and anchored into the bone at the point 21. A tightening device 29 is used to hold the rod 22 within sleeve 20. The exposed end of the rod 22 may be shaped to facilitate the use of a power or manual tool for insertion purposes, and the rod and/or sleeve may have a non-circular cross-section (such as the square shape shown) to minimize or prevent rotational variation once the sleeve is fitted over the rod.

Figure 2B:
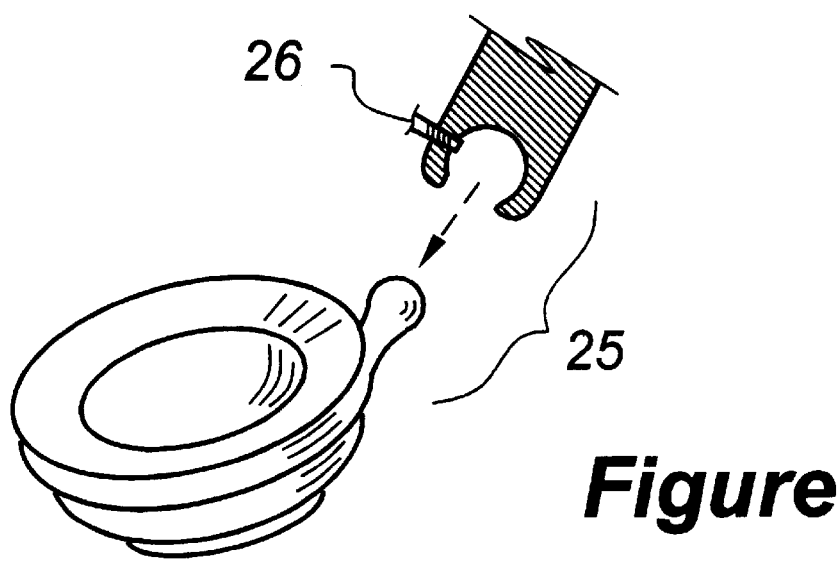
FIG. 2B provides a close-up look at an optional multi-degree-of-freedom joint which may be employed between an implant and an orienting member.
Figure 2A:
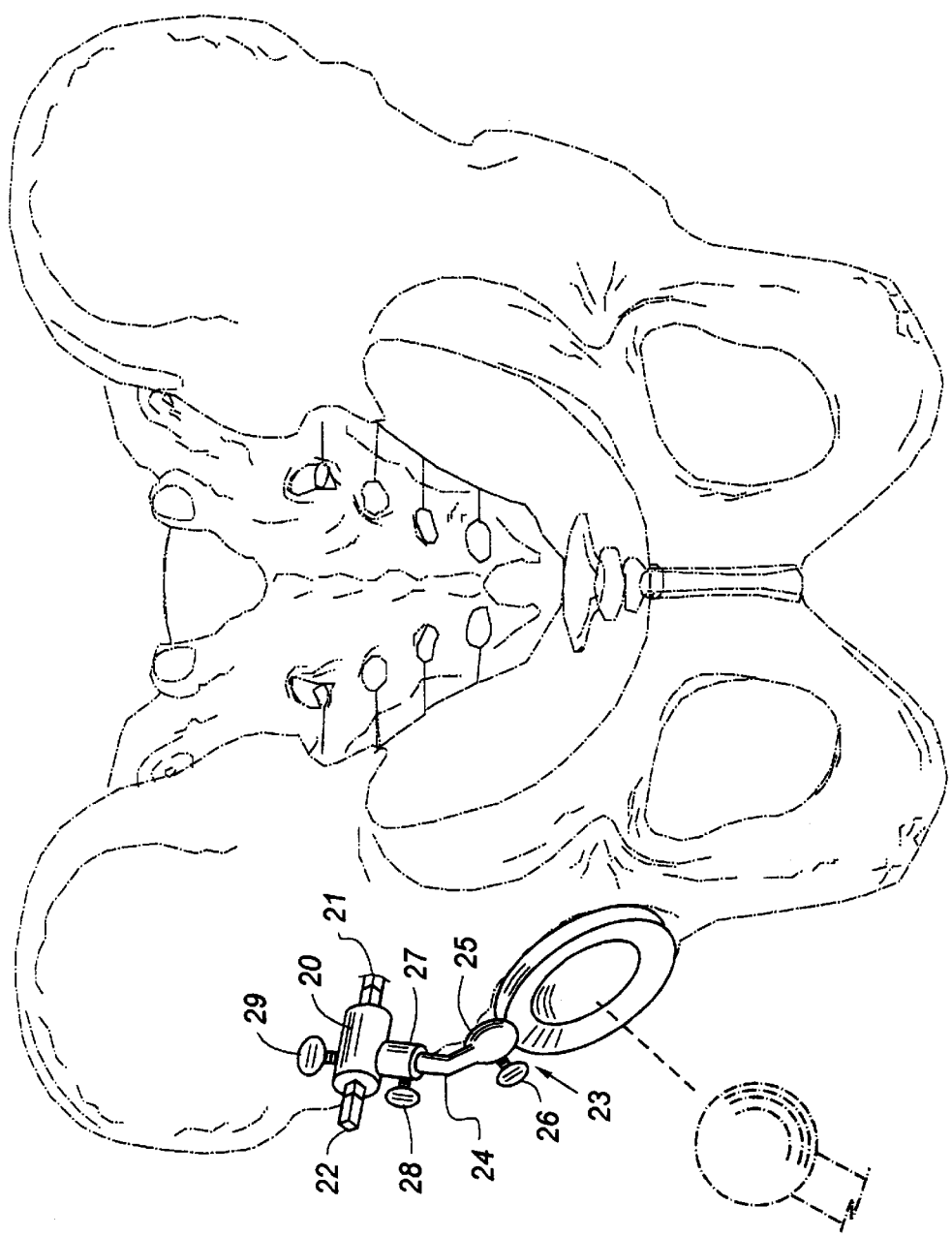
FIG. 2A illustrates how a trial or final implant may be oriented and installed using tools and techniques according to this invention.

The point 23 at which the connecting member 24 attaches to the implant includes an optional multi-degree-of-freedom joint 25, tightenable with a manually operable device such as thumb-screw 26, as best seen in FIG. 2B. Referring back to FIG. 2A, the connection between the member 24 and the anchoring unit may also be slidingly adjustable through the use of a collar 27 and tightening device 28. It will be appreciated that, as an alternative to the thumb-screws 26, 28 and 29, other tightening devices such as set screws, and other manually adjustable fasteners, may alternatively be utilized for such purposes.

According to a method aspect of the invention, the surgeon will typically first orient the implant with the anchoring device connected thereto, having prepared the bone cavity, as necessary. With the implant properly oriented, the anchoring unit may then be attached to the surrounding bone. In the alternative, the implant may first be oriented and the anchoring unit fixed to the surrounding bone, as discussed above. To accomplish this, one or more of the manually operated fastening devices, if present, may be loosened (or may have already been in a previously loosened state) to facilitate movement of the anchoring unit with respect to the implant or vice-versa. Whether before or after fixation of the anchoring device to the surrounding bone, the implant is aligned to as achieve a desired orientation. It will be appreciated that since the inventive apparatus is sufficiently low in profile, some or all of the pre-anchoring adjustment steps may be performed during a joint reduction. That is, with the femoral or ball portion of the joint engaging with the socket portion, as shown with the broken line in FIG. 2A.

With the orientation of the implant correctly positioned and rigidly coupled to the anchoring device now connected to the bone, in the preferred embodiment the implant may be temporarily removed, cement applied into the cavity, and replaced for fixation upon curing of the cement. This convenient aspect of the invention is shown in FIGS. 1 and 2. For example, with the manual tightening device 29 unloosened, the entire assembly may slip off of the rod 22, and be later reinstalled with the same, desired orientation. In the event that the implant was a trial and not a final implant, the implant may be replaced with the final, prior to the application of cement, and, if the same connection arrangement used with the trial is used in conjunction with the final implant, the inventive apparatus will automatically physically track the desired orientation upon reinstallation and cementation of the final.

To assist in holding the implant in place, a clamp may be provided with opposing jaws to apply pressure against the body of the implant (e.g., at the bottom of the socket), and an opposing, outer surface at the back of the pelvis (not visible in the figures). For example, a properly shaped "C"-type clamp may be utilized for such a purpose. Those of skill in the art will recognize that, as a further convenience, since the entire assembly is held into place during cement fixation, the surgeon may tend to other procedures while the cement is curing, for example, attention may be directed to the femoral aspect of the joint in the event of a total hip operation.

Once fixation has occurred, the various components comprising the outrigger assembly, including the anchoring device, are disengaged and removed. In the event that a small protrusion remains on the implant as part of the universal joint depicted in FIG. 2B, such protrusion may simply be left on the implant, if small enough in size. As an alternative, particularly if the implant is made of a softer material such as polyethylene, any vestisual structures associated with the invention may simply be cutoff using, for example, the surgeon's bone-cutting saw.

Figure 3:
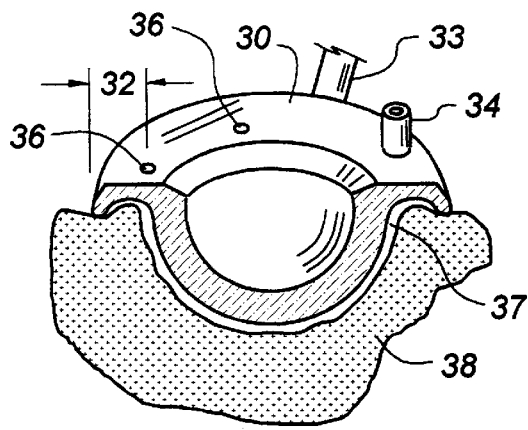
FIG. 3 is a drawing which illustrates an alternative trial or final implant according to the invention which enables cement to be pressurized with the implant in place.

FIG. 3 illustrates a further alternative embodiment of the invention wherein an implant 30 includes an outer lip 32 adapted to overlap and cover the rim surrounding the socket portion of the bone as shown. In this configuration, with the implant anchored to proximate bone through an outrigger 33, cement may be injected through a first port 34 and expelled through one or more exit ports 36 to create a uniform mantle of cement in the cavity 37. That is, with the socket reamed according to the shape of the outer hemisphere of the implant, a uniformly spaced region may be created, to realize a cement layer of uniform thickness. In the preferred embodiment of this arrangement, the exit port(s) 36 are of the type which release according to a predetermined amount of pressure, thereby ensuring a desired, uniform pressurization of the cavity 37.

Figure 4:
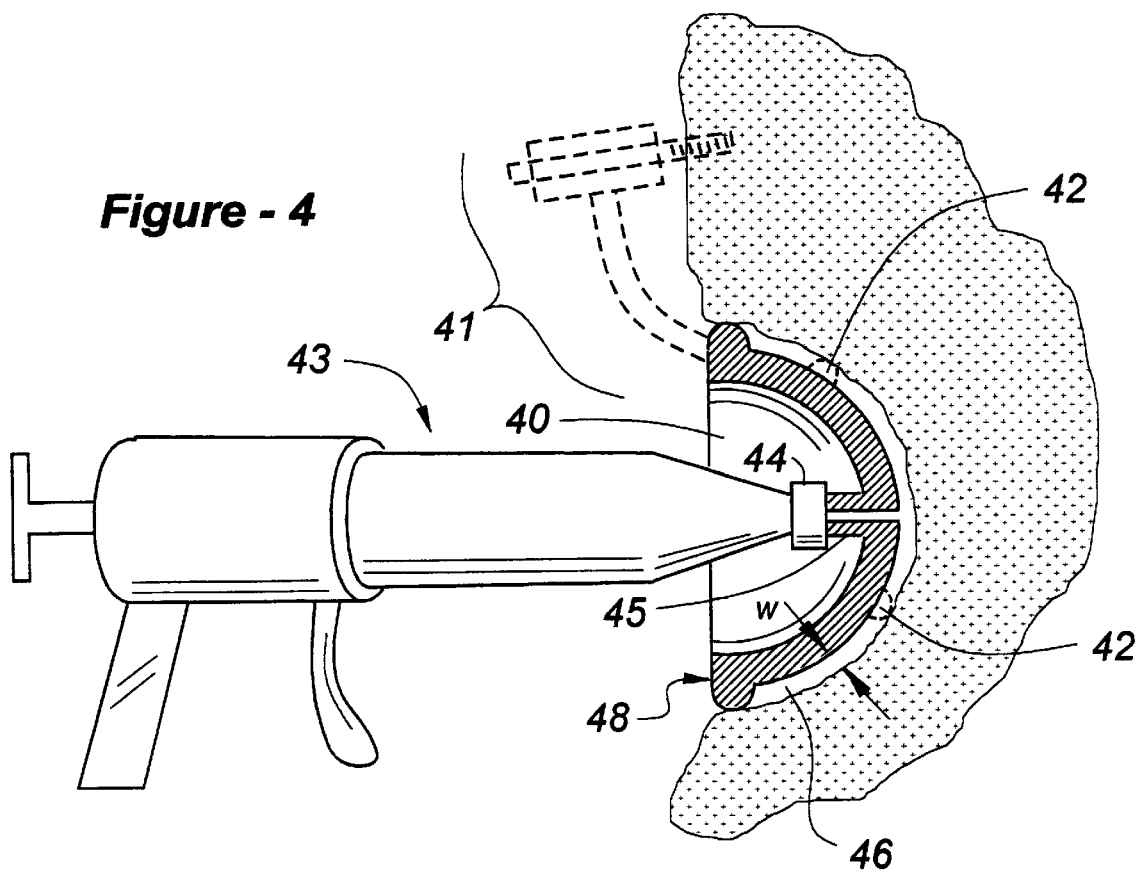
FIG. 4 is a drawing which shows an alternative cement-injection device according to the invention.

Turning now to FIG. 4, there is shown an embodiment of the invention wherein a device 40 having at least a partial implant shape, may be inserted into a region configured to received a prosthesis element, and to which a cement injector 43 may be coupled via connector 44 to an apertured stem 45, enabling cement to enter into and fill a cavity 46 created between the unit 40 and the surface of the bone. Preferably, the unit 40 is spaced apart from the bone by a width W which, when the unit 40 is removed and a final implant inserted into the cement bed, an appropriate thickness of cement mantle is created with a substantial uniform thickness and little or no loss.

To assist in determining a desired orientation in conjunction with cementation, the implant may include temporary or permanent spacer material with respect with its outer surface, such that when seated, a cavity is left which corresponds to the cement which will ultimately be used for fixation. In the case of a trial (or final) the outer surface may include spaced-apart protrusions 42 having a height equal to the thickness of the desired cement mantle or in the alternative, a resilient layer of rubber, for example, may be placed on the outer surface to approximate the thickness of the cement mantle. In the case of a trial, such a resilient layer may be permanent, since the trial will be removed and replaced with a final, whereas, in the case of a final, a removable resilient outer layer may be used during trialing which may then be removed or peeled off prior to cementation. The use of a peel-off layer also helps to ensure that the outer surface of the final if used for trialing purposes remains clean to accept the cement.

Different techniques may be utilized to ensure this positioning of the unit 40 relative to the bone, including an outrigger 41 of the type described above, or, alternatively or in conjunction with such assembly 41, protrusions 42 may be included to ensure this spacing. Cement relief ports may be provided on a rim 48 which also assists in centering, and, though not visible in the figure, the rim 48 may be shaped in accordance with the situation on hand to better ensure against loss of cement. For example, in the embodiment of an acetabular cementation, the rim 48 may include some form of flap or shield to ensure that the so-called acetabular notch is appropriately covered during cement injection.

Having described my invention, I claim:

1. Apparatus for achieving a desired orientation of an acetabular implant, comprising:
   an acetabular implant;
   an anchoring mechanism for rigidly attaching the implant to a point of bone surrounding a region associated with receiving the implant, the anchoring mechanism including one or more fasteners which may be loosened to temporarily remove the implant once a desired orientation is achieved; and
   physical tracking means facilitating re-installation of the implant in accordance with the desired orientation following the temporary removal.

2. The apparatus of claim 1, further including one or more adjustment devices enabling the anchoring mechanism to be movably positioned prior to its rigid attachment to the surrounding bone with the implant positioned at the desired orientation.

3. The apparatus of claim 2, including a plurality of adjustment devices facilitating a multidimensional desired orientation of the implant.

4. The apparatus of claim 1, wherein the anchoring mechanism includes a sleeve which may be used for the delivery of a rod having a threaded portion adapted for removable insertion into the surrounding bone.

5. The apparatus of claim 1, wherein the implant is a final.

6. The apparatus of claim 1, wherein the implant is a trial.

* * * * *